US00PP13257P2

(12) United States Plant Patent
van Ruiten

(10) Patent No.: US PP13,257 P2
(45) Date of Patent: Nov. 19, 2002

(54) DAHLIA PLANT NAMED 'MELODY DORA'

(75) Inventor: Jan van Ruiten, Sassenheim (NL)

(73) Assignee: Gebr. Verwer, Lisse (NL)

( * ) Notice: Subject to any disclaimer, the term of this patent is extended or adjusted under 35 U.S.C. 154(b) by 0 days.

(21) Appl. No.: 09/925,251

(22) Filed: Aug. 10, 2001

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Dahlia plant named 'Melody Dora', characterized by its upright, somewhat outwardly spreading and rounded plant habit; freely branching habit, full and dense plants; freely flowering habit; decorative inflorescence form with inflorescences positioned just above the foliage; red and yellow bi-colored ray florets; excellent garden performance; and excellent inflorescence longevity.

2 Drawing Sheets

BACKGROUND OF THE INVENTION

The present Invention relates to a new and distinct cultivar of Dahlia plant, botanically known as *Dahlia hybrida* and hereinafter referred to by the name 'Melody Dora'.

The new Dahlia is a product of a planned breeding program conducted by the Inventor in Voorhout, The Netherlands. The objective of the breeding program is to create new compact Dahlia cultivars with freely branching growth habit, decorative inflorescence form, attractive ray floret colors, and good inflorescence longevity.

The new Dahlia originated from a cross pollination made by the Inventor in 1966 of two unnamed *Dahlia hybrida* selections, not patented. The new Dahlia was discovered and selected by the Inventor as a single flowering plant within the progeny of the stated cross grown in a controlled environment in Voorhout, The Netherlands, in the summer of 1997. The selection of this plant was based on its compact plant habit and attractive ray floret coloration.

Asexual reproduction of the new Dahlia by cuttings was first conducted in Voorhout, The Netherlands in the spring of 1998. Asexual reproduction by cuttings has shown that the unique features of this new Dahlia are stable and reproduced true to type in successive generations.

SUMMARY OF THE INVENTION

The cultivar Melody Dora has not been observed under all possible environmental conditions. The phenotype may vary somewhat with variations in environment such as temperature, daylength, light intensity, water and nutritional status without, however, any variance in genotype.

The following traits have been repeatedly observed and are determined to be the unique characteristics of 'Melody Dora'. These characteristics in combination distinguish 'Melody Dora' as a new and distinct Dahlia:

1. Upright, somewhat outwardly spreading and rounded plant habit.
2. Freely branching habit, full and dense plants.
3. Freely flowering habit.
4. Decorative inflorescence form with inflorescences positioned just above the foliage.
5. Red and yellow bi-colored ray florets.

6. Excellent garden performance.
7. Excellent inflorescence longevity.

Plants of the new Dahlia differ primarily from plants of the parent selections in ray floret coloration.

Plants of the new Dahlia can be compared to plants of the cultivar Gallery Pablo, disclosed in U.S. Plant Pat. No. 10,599. In side-by-side comparisons conducted in Lisse, The Netherlands, plants of the new Dahlia are taller and have longer internodes than plants of the cultivar Gallery Pablo. In addition, inflorescences of plants of the new Dahlia have yellow and red bi-colored ray florets whereas inflorescences of plants of the cultivar Gallery Pablo are salmon-orange with yellow-colored centers.

Plants of the new Dahlia are similar in ray floret color to plants of the cultivar Aloha, not patented. In side-by-side comparisons conducted in Lisse, The Netherlands, plants of the new Dahlia are more compact and have smaller inflorescences. In addition, plants of the new Dahlia are typically grown as a container plant whereas plants of the cultivar Aloha are typically grown for cut flower production.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph on the first sheet comprises a side perspective view of a typical flowering plant of 'Melody Dora' that was about four months old.

The photograph at the top of the second sheet comprises a close-up view of typical inflorescences of 'Melody Dora'.

The photograph at the bottom of the second sheet comprises a close-up view of a typical inflorescence of 'Melody Dora'.

DETAILED BOTANICAL DESCRIPTION

In the following description, color references are made to The Royal Horticultural Society Colour Chart except where general terms of ordinary dictionary significance are used.

The following observations and measurements describe plants grown and flowered during the summer and early autumn of 2000 in Lisse, The Netherlands, in an outdoor nursery and under conditions which approximate those generally used in commercial production. During the production of the plants, day temperatures ranged between 15 and 23° C. and night temperatures ranged between 10 and 15° C. Plants were pinched one time about three to four weeks after planting. Measurements and numerical values represent averages of typical flowering plants that were about four months old.

Botanical classification: *Dahlia hybrida* cultivar Melody Dora.

Parentage:

*Female, or seed, parent.*—Unnamed selection of *Dahlia hybrida*, not patented.

*Male, or pollen, parent.*—Unnamed selection of *Dahlia hybrida*, not patented.

Propagation:

*Type.*—By vegetative cuttings.

*Time to initiate roots.*—About five days at 17° C.

*Time to develop roots.*—About 14 to 17 days at 17° C.

*Root description.*—Fine, fibrous and well-branched.

*Tuber description.*—Shape: Fusiform. Clump diameter: About 15 cm. Color: Close to 199C, with anthocyanin, 59C.

Plant description:

*Appearance.*—Herbaceous flowering container or garden plant. Inverted triangle; stems mostly upright and somewhat outwardly spreading giving a rounded appearance to the plant. Freely branching, about 8 lateral branches develop after removal of terminal apex (pinching); dense and full plants.

*Crop time.*—About 70 days from planting are required to produce flowering finished plants.

*Plant height.*—About 65 cm.

*Plant width.*—About 40 cm.

*Lateral branches (peduncles).*—Angle: Erect to almost 45° from vertical. Strength: Strong. Length: About 10 to 20 cm. Diameter: About 8 mm. Texture: Smooth, glabrous. Color: 144A.

*Foliage description.*—Arrangement: Leaves opposite; leaves may be single or compound with three or five leaflets. Typically about 4 to 5 pairs of leaves per lateral stem. Shape: Ovate. Apex: Acuminate. Base: Attenuate. Margin: Serrate. Length: Single leaves: About 5 cm. Compound leaves with three leaflets: About 12.2 cm. Compound leaves with five leaflets: About 22 cm. Width: Single leaves: About 2.2 cm. Compound leaves with three leaflets: About 9 cm. Compound leaves with five leaflets: About 17.3 cm. Venation pattern: Pinnate. Texture: Smooth, glabrous; leathery. Color: Young and mature foliage, upper surface: 147A. Young and mature foliage, lower surface: 147B. Venation, upper surface: 144A. Venation, lower surface: 144B. Petiole length: Single leaves: About 1 cm. Compound leaves with three leaflets: About 2.4 cm. Compound leaves with five leaflets: About 2.5 cm. Petiole diameter: About 4 mm. Petiole color: Upper surface: 147B. Lower surface: 147A.

Inflorescence description:

*Appearance.*—Terminal inflorescences held just above the foliage on strong peduncles. Decorative inflorescence form with elongated ovate-shaped ray florets; ray florets arranged acropetally on a capitulum. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 35 days in an outdoor environment; and as cut flowers, inflorescences maintain good color and substance for about 7 days in an indoor environment.

*Quantity of inflorescences.*—One per lateral shoot, about 60 inflorescences plant develop during the growing season, summer through autumn.

*Inflorescence bud, at stage of showing color.*—Shape: Globular. Length: About 1.3 cm. Diameter: About 1.7 cm. Color: 151D.

*Inflorescences.*—Shape, in profile: Hemispherical. Diameter: About 12 cm. Depth (height): About 6.5 cm. Disc diameter: About 1 cm. Receptacle diameter: About 2.3 cm. Receptacle height: About 5 mm.

*Ray florets.*—Shape: Elongated-ovate. Orientation: Initially upright, outer florets perpendicular to peduncle. Apex: Acute. Base: Attenuate; short corolla tube. Margin: Entire. Aspect: Intially concave to mostly flat. Length: About 5.6 cm. Width: About 2.2 cm. Texture: Smooth, glabrous; satiny. Number of ray florets per inflorescence: About 220 in about 23 rows. Color: When opening, upper and lower surfaces: Towards base, 6B; towards apex, 64A. Fully opened, upper surface: Ground color, 6B; towards the apex, overlain with 42A; ground color fading to 2A with subsequent development. Fully opened, lower surface: Ground color, 2C; towards apex, underlain with 64C.

*Disc florets.*—Number of disc florets per inflorescence: About 20. Shape: Tubular, elongated. Apex: Five-pointed. Length: About 1.5 cm. Width: Apex: About 4 mm. Base: About 1.8 mm. Color: Immature: 157C. Mature: Apex: 8A. Mid-section: 16C. Base: 157D.

*Phyllaries.*—Quantity: One whorl of about 6 phyllaries. Shape: Ovate. Apex: Acute. Base: Attenuate. Margin: Entire. Length: About 1 cm. Width: About 3 mm. Texture: Smooth. Color: Upper surface: 146B. Lower surface: 146B, with anthocyanin, 183B.

*Reproductive organs.*—Androecium: Present on disc florets only. Stamen quantity: About 15 per floret. Anther length: About 5 mm. Anther color: 9B. Pollen amount: Scarce. Pollen color: 8C. Gynoecium: Present on ray and disc florets. Pistil quantity: About 15 per floret. Pistil length: About 6 mm. Stigma color: 14A. Style length: About 2 mm. Style color: 154D. Ovary color: 2C.

*Seeds.*—Length: About 6 mm. Color: 200B.

Disease resistance: Resistance to pathogens common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Melody Dora', as illustrated and described.

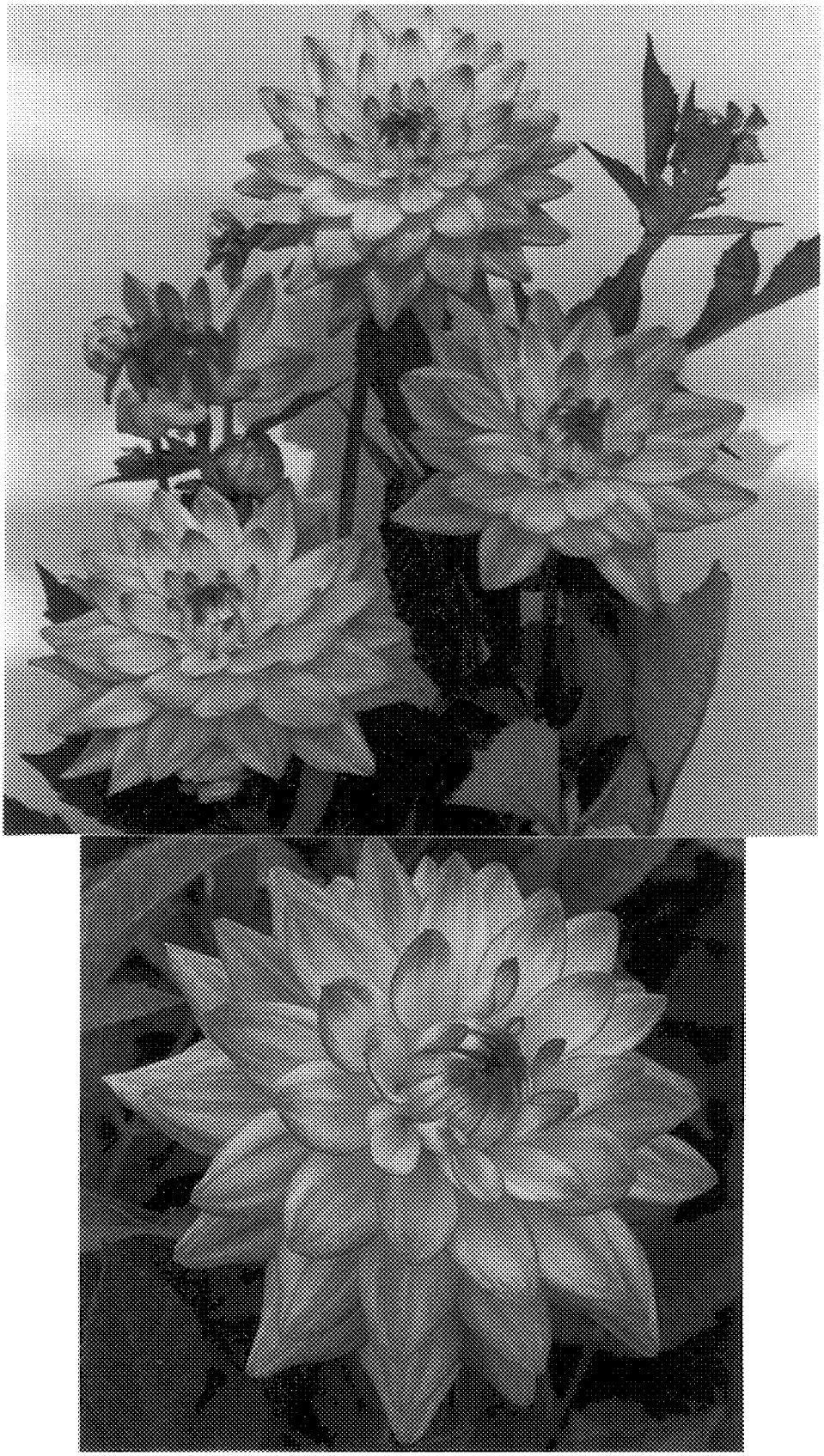

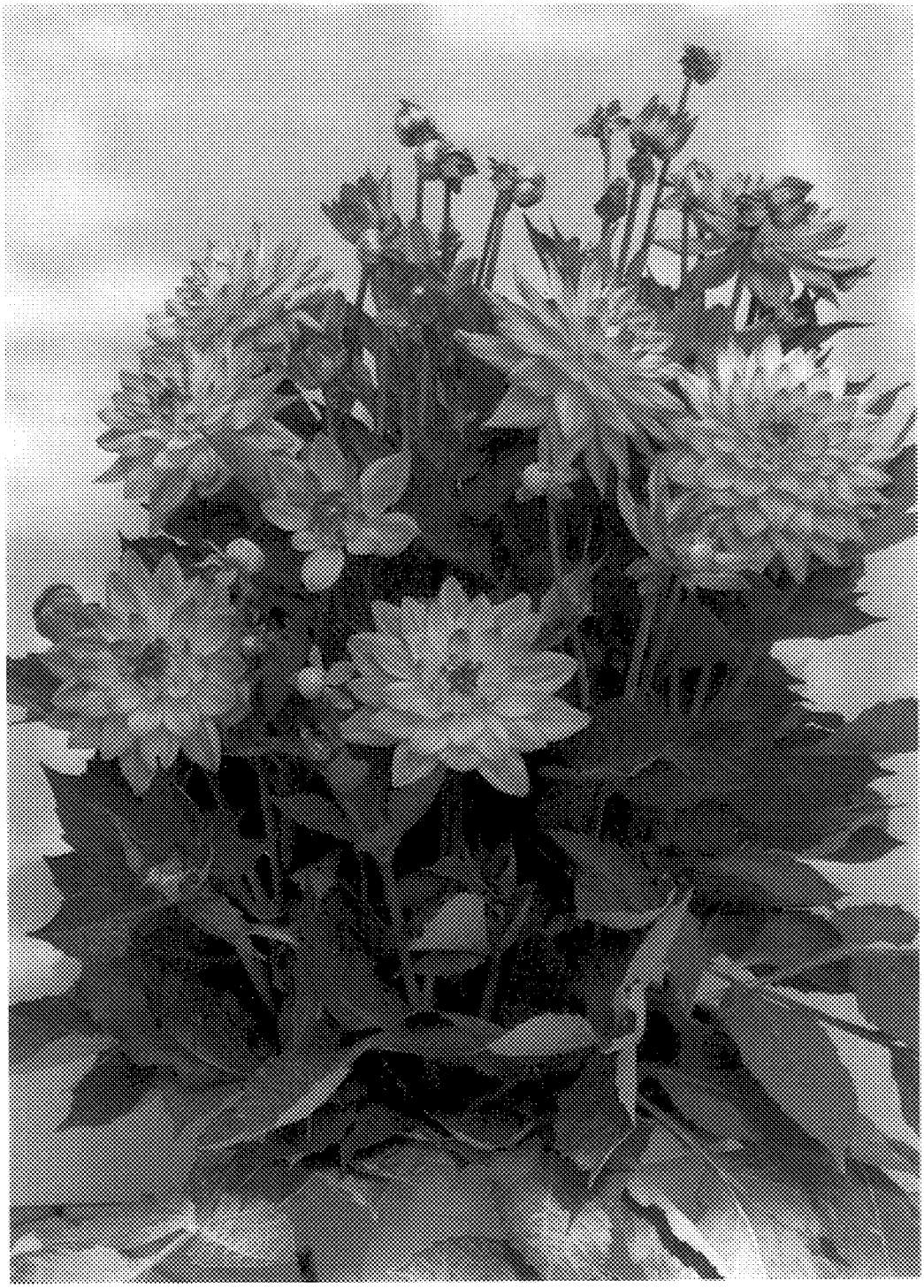

* * * * *